United States Patent [19]
Cami et al.

[11] Patent Number: 6,147,259
[45] Date of Patent: Nov. 14, 2000

[54] PROCESS FOR PRODUCING GLUTAMIC ACID

[75] Inventors: Pierre Cami, Languevoisin, France; Aharon Eyal, Jerusalem, Israel

[73] Assignees: Amylum N.V., Aalst, Belgium; A. E. Staley Manufacturing Company, Decatur, Ill.

[21] Appl. No.: 09/101,457

[22] PCT Filed: Jan. 21, 1997

[86] PCT No.: PCT/GB97/00177

§ 371 Date: Oct. 7, 1998

§ 102(e) Date: Oct. 7, 1998

[87] PCT Pub. No.: WO97/27170

PCT Pub. Date: Jul. 31, 1997

[30] Foreign Application Priority Data

Jan. 22, 1996 [IL] Israel ........................................ 116848

[51] Int. Cl.[7] ........................ C07C 229/24; C07C 229/00
[52] U.S. Cl. .............................................................. 562/573
[58] Field of Search ............................................. 562/573

[56] References Cited

U.S. PATENT DOCUMENTS

| | | | |
|---|---|---|---|
| 3,015,655 | 1/1962 | Stark et al. | 260/211.5 |
| 3,325,539 | 6/1967 | Conklin et al. | 260/527 |
| 3,336,374 | 8/1967 | Dobry | 260/527 |
| 3,505,399 | 4/1970 | Samejima et al. | 260/527 |
| 3,639,467 | 2/1972 | Nagal et al. | 260/527 |
| 3,655,746 | 4/1972 | Shiraishi et al. | 260/527 |
| 4,675,196 | 6/1987 | Villa et al. | 426/271 |
| 5,279,744 | 1/1994 | Itoh et al. | 210/676 |

FOREIGN PATENT DOCUMENTS

| | | | |
|---|---|---|---|
| 1591950 | 6/1970 | France . | |
| 6-17346 | 1/1994 | Japan . | |
| 401 987 | 5/1966 | Switzerland . | |
| 700803 | 11/1979 | U.S.S.R. . | |
| 811688 | 4/1959 | United Kingdom . | |
| 1 201 823 | 8/1970 | United Kingdom . | |
| 2 095 232 | 9/1982 | United Kingdom | C07C 101/22 |
| WO 97/27170 | 7/1997 | WIPO . | |

OTHER PUBLICATIONS

Mitsubishi's Diaion Manual of Ion Exchange Resins and Synthetic Adsorbents (Mar. 1992), pp. 71–72.

Z. Jiang et al., "Recovery of Glutamic Acid from Fermentation Broth by Ion Exchange Process", Lizi Jiaohuan Yu Xifu 3(4) 35–9 (1987) No Month Provided.

*Primary Examiner*—Johann Richter
*Assistant Examiner*—Rosalynd Keys
*Attorney, Agent, or Firm*—Foley & Lardner

[57] ABSTRACT

An indirect acidulation process for producing glutamic acid from an aqueous feed containing a glutamate resulting from fermentation includes: a) contacting an aqueous feed stream at an elevated temperature with a weak acid cation exchanger (WACE) which is at least partially in its acid form, whereby a part of the cations in the solution is taken up by the cation exchanger and protons are introduced into the solution; b) contacting a second aqueous feed containing glutamate and cations at an elevated temperature with a strong acid cation exchanger (SACE) that is obtained from a subsequent step and carries cationic glutamate, whereby the cationic glutamate is transferred into the solution and most of the cations in the second aqueous feed are taken up by the SACE; c) crystallizing glutamic acid from the effluent of step (b); d) contacting the mother liquor of step (c) with the SACE which is at least partially in its acid form whereby cationic glutamate is bound; e) utilizing the SACE obtained in step (d) in step (b); f) regenerating the SACE from step (b) to its at least partially acid form by a solution of a strong acid and utilizing the SACE in its at least partially acid form in step (d) while forming an effluent containing an acidic solution of salts, comprising cations bound to the cation exchanger in step (b) and the anions of the strong acid; g) regenerating the WACE from step (a) to its at least partially acid form by the effluent from step (f) and utilizing the WACE in its at least partially acid form in step (a) while forming an effluent containing a solution of salts, comprising cations bound to the cation exchangers in steps (a) and (b) and the anions of the strong acid; and h) directing the salt solution obtained as the effluent of step (g) for commercial use.

23 Claims, No Drawings

PROCESS FOR PRODUCING GLUTAMIC ACID

The present invention relates to a process for producing glutamic acid. More particularly, the present invention relates to an indirect acidulation process for the preparation of glutamic acid and monosodium glutamate (hereinafter referred to as MSG), from a glutamate-containing aqueous feed resulting from fermentation.

Many patents propose using ion exchangers in the separation of amino acids in general, and particularly for production of glutamic acid and mono-sodium glutamate. In some cases, the ion-exchangers are used for removal of anionic and cationic impurities. In others, glutamic species are bound on the resin. In basic medium glutamate carries one or two negative charges and can be bound to an anion exchanger. In strongly acidic solution (pH of about 2 or lower), the glutamate is positively charged and binds to cation exchangers.

U.S. Pat. Nos. 3,336,374 and 3,655,746; and GB 2,095,232 use cation and anion exchangers for removal of contaminants. In U.S. Pat. No. 3,015,655 nitrogenous organic compounds, including amino acids, are bound to a strongly acidic cation exchanger (SACE). British Patent 811,688 purifies solutions containing glutamic acid by ion-exchangers and then binds the glutamic acid to a weakly basic anion exchanger (WBAE), U.S. Pat. No. 5,279,744 uses SACE for binding glutamic acid in multiple-counter current stages. JP 94017346 separates giutamic acid on SACE with the improvement of adding urea to prevent the growth of amino acid crystals on the resin and to enable a smooth elution. U.S. Pat. No. 4,675,196 removes glutamic acid from amino acid mixtures, obtained on protein hydrolysis, by adsorption on a strong base anion exchanger (SBAE). U.S. Pat. No. 3,505,399 adsorbs glutamic acid from an acidic solution of pH=2.0–0.5 on a SACE and elutes it with alkaline solution. CN 91-104354 suggests adsorption of glutamic acid from crystallization mother liquor with an ammonium- type SACE and elution with ammonia water.

The glutamate adsorption steps are followed by elution with various eluants, typically mineral acids or bases, so that the eluted glutamic acid is obtained in its salt form, or in a mixture with another acid. The effluent from the elution step requires further treatment for recovery of the acid, or for purification of the salt.

According to GB 1201823, glutamic acid is recovered by passing a mother liquor (having a pH<4 from which some of the glutamic acid originally present has been crystallized and separated) through a strongly acidic cation exchange resin. Glutamic acid is adsorbed by the resin and is eluted with a fresh, glutamic acid containing fermentation broth. The eluate pH is adjusted to crystallize glutamic acid, which is then separated.

CH 401 987 teaches a process for the extraction and purification of glutamic acid from a liquid containing the same. Cationic impurities are eliminated by passing the liquid through a weakly acidic cation exchanger (WACE). Anionic and non-ionic impurities are separated by the use of a SACE. Glutamic acid is then eluted from the SACE with aqueous alkali; the pH is then adjusted and glutamic acid crystallised out.

SU 700803 suggests separation of the cells from the broth which is then passed through 2 columns of cation exchange resins and the glutamic acid is eluted with $NH_4OH$. The latter is passed through the first columns successively. The eluate is acidifed to pH=3.2 to separate crystals of glutamic acid. To increase the purity of the product, the eluate from the first column is cooled and acidified. The crystals of glutamic acid are separated and the solution is passed through the second column.

The eluate from the second column is treated in the same way and the crystals of glutamic acid separated in both steps are mixed together. Glutamic acid separated by crystallization in the first step is dissolved in $NH_4OH$ solution (used for the regeneration of the ion exchangers) and recrystallized after evaporation and acidification of the solution. To simplify the regeneration of ion exchanger re sins a mineral acid was passed through the columns.

U.S. Pat. No. 3,325,539 describes a method for separating glutamic acid and salts thereof from a fermentation broth containing the same and solid materials, which method comprises passing fermentation broth containing glutamic acid, salts thereof, and solid materials upflow through a bed of strongly acidic cation exchange resin on the hydrogen cycle at a rate sufficient to expand the bed between 1.05 and 1.6 times its original depth, thereby adsorbing glutamic acid on said resin; discontinuing the flow of fermentation broth over said resin; and eluting said adsorbed glutamic acid from said resin with a 0.5–2 N sodium hydroxide solution.

In said patent it has been discovered that fermentation broth containing glutamic acid and salts thereof, and solid material, may be submitted directly to ion exchange treatment, without filtering the fermentation broth prior to exchange procedure, by flowing the unfiltered fermentation broth upflow through an expanded bed of appropriate ion exchange material. The specifications of required expansion degree and flow rates are discussed there. As a result, essentially all of the solid material present in the broth passes through the voids created by the expansion, and flows out of the top of the resin column with the effluent stream. There is no plugging of the resin bed due to the accumulation of solid material.

According to said Patent, as the fermentation broth contacts the cation exchange resin essentially all the cations and glutamic acid present in the broth are adsorbed onto the resin. Then the column and resin bed are washed with water to remove residual solids, and then the column is heated to a temperature of from 40 to 60° C. Then elution is conducted by 0.5–2N warm NaOH solution.

This elution scheme is presented as an improvement, resulting in a "considerable purity". Yet, although in most cases sodium glutamate is the desired product and sodium glutamate is the "considerably pure" component in the eluate, the inventors do not suggest its recovery from the eluate through crystallization. instead, an acid is added in an amount equivalent to the sodium glutamate, to adjust the pH to glutamic acid isoelectric point and to precipitate glutamic acid. This results in al consumption of additional reagents; b) production of an undesired by-product salt; and c) a co-precipitation of impurities with the glutamic acid due to the salting out effect of the by-product salt.

The cation exchange resins employed in the process of U.S. Pat. No. 3,325,539 are strongly acidic. After the elution by NaOH, they are loaded with sodium resulting from the eluent and by the cations present in the fermentation liquor. For reuse in the process they have to be converted to their acidic form by washing them with a strong acid. As the resins are strongly acidic, the resulting effluent would be acidic too, containing an excess of acid in the case of monoprotic acid, or an acidic salt in the case of multiprotic acid. This acidity would need neutralization prior to disposal of the effluent.

Let us assume that NaOH was used as the neutralizing agent in the fermentation and that sulfuric acid is used as the acidulant of the eluate and for resin regeneration. Let us also assume that the fermentation broth is free of other salts. In that case the reactions in the overall process are:
1. HGA+NaOH→NaGA (fermentation)
2. $2RSO_3H+NaGA→RSO_3-Na^++RSO_3-H_2GA^+$ (adsorption)
3. $RSO_3-Na^++RSO_3-H_2GA^++2NaOH→2RSO_3-Na^++NaGA$ (elution)
4. $NaGA+½H_2SO_4→½Na_2SO_4+HGA$ (glutamic acid recovery)
5. HGA+NaOH→NaGA (sodium glutamate formation)
6. $2RSO_3-Na^++2H_2SO_4→2RSO_3H+2NaHSO_4$ (resin regeneration)
7. $2NaHSO_4+2NaOH→2Na_2SO_4$ (effluent neutralization)
8. $HGA+6NaOH+2.5H_2SO_4→NaGA+2.5\ Na_2SO_4$ Five equivalents of NaOH and of sulfuric acid are consumed and five equivalents of by-product salt are formed.

A conventional process for glutamic acid recovery from fermentation liquors is acidulation of the broth by a mineral acid, usually $H_2SO_4$, to pH of about 3.2 and crystallization of glutamic acid therefrom.

The mother liquor contains the salts and other impurities present in the fermentation liquor and the salt formed on displacing glutamic acid from its salts, usually ammonium sulfate. The broth concentration in this operation is quite high to assist, along with the salting out effect of the salt, in recovering most of the glutamic acid. Yet a significant amount of glutamic acid is still left in the mother liquor, requiring complex and costly steps for its recovery.

In French Patent 1,591,950, British Patent 1,201,823 and U.S. Pat. No. 3,639,467 an improvement to this process is proposed. The glutamic acid containing mother liquor is passed over a strong acid cation exchanger in the acid form. The glutamic acid is separated from the mother liquor by binding to the cation exchanger. The latter is then eluted by fermentation liquor. The pH of the eluate containing the liberated glutamic is adjusted to 3.2 and glutamic acid is crystallized. The eluted resin carries now cations and is regenerated by a strong acid, i.e., as in equation (6). Due to the recovery of glutamic acid from the mother liquor, the losses are low and the mother liquor does not need to be concentrated, reulting in purer crystals of acid.

Only strong acid resin could work in this process, and as a result excess acid and effluent neutralization are required as in the case of USP 3,325,539.

Glutamic acid is recovered presently from contaminated aqueous solutions comprising its salt (MGA) by acidulation with a strong mineral acid (HX) to form a salt of the mineral acid and the cation of the glutamic acid salt (MX) and liberated glutamic acid (HGA). In order to reduce the amount of HGA left in the mother liquor, the feed contaminated aqueous solution is concentrated prior to the acidulation. As a result, the liberated glutamic acid is crystallized from a concentrated solution comprising also the salt formed (MX) and the contaminants (resulting in most cases from fermentation). In these conditions the purity of the crystallized HGA is not sufficient and additional purification steps are required. The mother liquor still contains HGA along with MX and other compounds which are contaminants for glutamic acid, but are valuable as components of animal feed. As a result the mother liquor goes through a large number of separation steps to recover these components separately and in as pure a form as possible. These separations, as well as the additional steps for HGA purification, are expensive in equipment, energy and reagents (mainly due to the large recycles in the system).

HGA is crystallized at a pH of about the isoelectric point (1P) where glutamic acid is in its zwitterionic form, $HOOCH_2CH_2CH(NH_3+)COO^-$. At lower pH it is protonated to its cationic form $HOOCH_2CH_2CH(NH_3+)COOH$. In this form it can be bound to a cation exchanger. Thus, HGA can be recovered from mother liquor by binding to a cation exchanger. Higher yields were claimed for such binding, reducing HGA losses. The aqueous solution, from which HGA is crystallized, does not need to be as concentrated as above, but still comprises the salts formed on acidulation. The mother liquor after HGA adsorption still comprises a mixture of salts and animal feed components.

According to French patent 1,591,950, the cation exchanger that carries the cationic glutamic acid is eluted by the fermentation liquor. Cations present there displace the cationic glutamic acid into the solution and are bound instead. The cations loaded cation exchanger is eluted by a mineral acid and the cation exchanger is converted into its acidic form that can bind glutamic acid from the mother liquor of its crystallization. In such a process part of the acidulation by a strong mineral acid is, in fact, conducted indirectly. Cations from the solution are bound to the cation exchanger which thereby acidulates the solution. Part of the acidulating mineral acid is applied on the cation exchanger rather than being added directly to the solution.

This indirect acidulation is not discussed as such in the prior art found. Its advantages are clear: The amount of salt in the solution fed to HGA crystallization is lower and some of the salt is obtained in a stream free of the valuable animal feed components. It would be obvious to consider conducting substantially all the acidulation indirectly, i.e. binding most of the cations in the feed to the cation exchanger, which would then be regenerated by a strong acid. This would maximize the above-listed advantages.

None of the prior art describes or claims practically complete indirect acidulation. One could argue that it is implied by some of the patents, but that is not necessarily the case. One must keep in mind that the advantages of this practically complete indirect acidulation would seem to be out-balanced by a major disadvantage - a huge excess of acid and base consumption over the direct acidulation.

The cation exchanger used for glutamic acid binding from the mother liquor should, according to the prior art, be a strong acid, e.g. a resin carrying sulfonic acid type groups. It has to be strongly acidic to prefer the cationic glutamic acid over protons present in large concentrations in the acidulated mother liquor. Transforming such strongly acidic cation exchangers from its cations carrying form back to its acid form requires high acidity in the regenerating solution as explained by Mitsubishi's Diaion Manual of Ion Exchange Resins and Synthetic Adsorbents (March 1992): "Strongly acidic cation exchange resins are difficult to regenerate on account of their strong acidity, and more regenerating agent is required than the theoretical exchange capacity." This manual shows the relationship between the amount of HCl used and the break-through exchange capacity of a SACE: regeneration of exchange capacity to 1 eq/l and 1.5 eq/l require about 2 eq/l and about 4.5 eq/l of HCl respectively. Therefore, regeneration of strong acid cation exchanger (SACE) by $H_2SO_4$ results in bisulfates. Thus, practically complete indirect acidulation using SACE would require a double amount of sulfuric acid compared to the direct acidulation and would form an acidic effluent. For most outlets this effluent would need base addition for neutralization.

It has now been surprisingly found according to the present invention that a weak acid cation exchanger WACE is strong enough for achieving, in a combination with a SACE, a practically complete indirect acidulation without resorting to a significant excess of acid in the combined regeneration. This finding is surprising in view of the pka's involved. The WACE carry carboxylates as functional groups (RCOOH) and the acidulation should follow the reaction:

RCOOH +NH$_4$++$^-$OOCCH$_2$CH$_2$CH(NH$_3$+)COO$^-$=RCOO$^-$ NH$_4$++HOOCCH$_2$CH$_2$CH(NH$_3$ +)COO$^-$

For such reaction to take place the acidity of the resin should be higher than that of the glutamic acid carboxylate to be protonated, or of a similar acidity. Yet, even the weaker carboxyiate of the glutamic acid is quite a strong acid, pKa=4.25. The carboxylates of the resin are significantly weaker acids. According to the Mitsubishi Manual, the pKa of methacrylic type WACE is about 6 and that of the acrylic type is 5.3. Thus, even the stronger WACE is an order of magnitude weaker than the weaker carboxylate of glutamic acid and one would not expect any significant acidulation. The same manual states:

"As the exchange group of the resin, the carboxyl group is only weakly acidic, it does not dissociate in acid solution and there is no ion exchange ability. The same is true in neutral salts . . . " This again teaches away from any ability to acidulate a neutral glutamate salt feed solution. Furthermore, the manual proposes the combination of WACE and SACE, for the regeneration section, but even there it is not very attractive: "as they can even be regenerated by the regeneration effluent from the strongly acidic cation exchange resin, regenerant is often economized by combining the two types of resin. However, this ease of regeneration is offset by the ease with which they lose their captured ions, and even a flow of water may be sufficient to hydrolyse them and elute the ions in the water."

The surprising efficiency of WACE in indirect acidulation allows the process of the present invention as hereinafter defined to combine the application of WACE and SACE. This combination provides some important improvements compared to the prior art:

a. high purity of the crystallized glutamic acid;
b. high recovery yields;
c. substantially stoichiometric consumption of acid and base;
d. The salts are obtained in a separate, concentrated stream providing for easier recovery for utilization; and
e. The organic matter in the aqueous feed to the process is obtained in a stream essentially free of salts and are easily recovered for application as animal feed components.

Thus, according to the present invention, there is now provided an indirect acidulation process for producing glutamic acid from an aqueous feed containing glutamate resulting from fermentation, comprising the steps of:

a. contacting said aqueous feed stream at an elevated temperature with a weak acid cation exchanger (WACE) in its acid form whereby part of the cations in the solution is taken up by the cation exchanger and protons are introduced into the solution.
b. contacting an aqueous feed containing glutamate at an elevated temperature with a strong acid cation exchanger (SACE) that is obtained from a subsequent step and carries cationic glutamate, whereby the cationic glutamate is transferred into the solution and most of the cations are taken up by the SACE.
c. crystallizing glutamic acid from the effluent of step (b).
d. contacting the mother liquor of step (c) with SACE in its acid form whereby cationic glutamate is bound.
e. Transferring the SACE obtained in step (d) to step (b).
f. regenerating the SACE from step (b) to its acid form by a solution of a strong acid and transferring the SACE in its acid form to step (d) while forming an effluent containing an acidic solution of salts, comprising cations bound to the cation exchanger in step (b) and the anions of the strong ac id.
g. at least partially regenerating the WACE from step (a ) by the effluent from step (f) and transferring the WACE in its acid form to step (a) while forming an effluent containing a solution of salts, comprising cations bound to the cation exchangers in steps (a) and (b) and the anions of the strong acid.
h. directing the salt solution obtained as the effluent of step (g) for commercial use.

In preferred embodiments of the present invention said aqueous feed which is contacted with the SACE in step (b) comprises effluent from step (a).

Jiahg Zhixin et. al (Lizi Jiaohuan Yu Xifu (1987), 3(4) 35-9) have considered partial indirect acidulation prior to direct acidulation by a mineral acid. They have tested for that purpose two cation exchangers in the acid form, type 110 and type D152. These cation exchangers are described as being weak, but their functional groups and the matrix composition are not described. These cation exchangers were tested for NH$_4$+ adsorption from ammonium glutamate solution of initial pH=6.05 and NH$_4$+ concentration of 0.454%. The results are described in terms of the limits of ammonium ion removal from the solution. Those were about 30% and about 15% for type 110 and type D152, respectively. The limits were even lower when the starting pH was 5.18. In another experiment the authors have tested the effect of solution pH on the exchangers' capacity for ammonium. As expected, the capacity dropped on lowering the pH. It is very important to note that the lowest pH tested in this experiment was 4.42, which is about 0.2 logarithmic units above the second pKa of glutamic acid.

The results presented by the authors seem therefore to indicate that it is not possible to attain a practically complete indirect acidulation by a combination of WACE and SACE, whereby at least about 50% of the acidulation is conducted by the WACE. This article thus indicates that use of high excess of acid in the regeneration is not avoidable.

As a consequence, the authors propose a complicated process comprising the operations of partial indirect acidulation by a WACE, followed by direct acidulation to the isoelectric point by a mineral acid, and then recovery of glutamic acid from the mother liquor by a SACE. The SACE is eluted by NaCH rather than contacted with an aqueous feed as in step (b) of the present invention, and is regenerated by HCl. An excess of HCl is required to regenerate the SACE.

Suitable SACE are resins carrying a strong acid functional group. Particulary useful are those carrying sulfonic groups, e.g., Dow's XUS 40406 and Dowex$^{(R)}$ MSC-1 Rohm and Haas' Amberlite$^{(R)}$ 200C, JR 120, 122, 132 and 252; Purolite's C-100, 120, 145, 150 and 160; and Mitsubishi's Diaion$^{(R)}$ SK and pK series. Suitable WACE usually carry a carboxylate group, e.g. Rohm and Haas' Duolite$^{(R)}$ C470; IRC 50, 76 and 86; Purolites$^{(R)}$ C105, 106, 107 and 115$^{(R)}$; and Mitsubishi's Diaion$^{(R)}$ WK 10, 11 and 20. The resins could be of a gel or a (macro) porous type, with styrenic, methacrylic or acrylic polymer matrix, with various degrees of cross-linking. For the WACE the acrylic type is preferred.

The glutamate-containing aqueous feed treated in the process contains salts of glutamic acid, e.g., monosodium and monoammonium glutamate, as well as various contaminants, such as other salts, resulting from ions present in the carbohydrates fed to the fermentation or from the nutrients, carboxylic and amino acids, carbohydrates and non-fermentables. It might also contain relatively low levels of glutamic acid. The glutamate/glutamic acid in the feed stream results from fermentation. The feed could be a fermentation liquor, a side stream from another fermentation liquor treament, a recycle stream from a successive step, or various mixtures of these. Thus, glutamic acid produced in the proposed process could be neutralized by NaOH to form a solution from which monosodium glutamate (MSG) is crystallized. While the glutamic acid produced in the process is of high purity, it still contains some impurities that would concentrate in the mother liquor of MSG crystallization. In order to avoid contamination of the product, some of the mother liquor is bled out. This contaminated bleed can be fed to the process as such, or in a mixture with other streams. The feed could also be a mother liquor of MSG production by other methods.

The glutamate-comprising aqueous feed can undergo some pretreatments. It was found, however, that cell removal from it is not needed. The cells introduced would end up in the effluent of step (d), and therefore can preferably be used as part of animal feed components. Other glutamic acid/MSG processes require pre-removal of cells. Complete removal from the total amount of the broth is expensive. Therefore said glutamate-containing fermentation liquor can be preferably treated to form two streams, a first stream substantially free of cells and second stream comprising most of the cells present initially in the fermentation broth, said second stream being fed as the aqueous feed stream to step (a).

As described above, one of the advantages of the present process is that the crystallization of glutamic acid is made from a diluted solution with low salt content, providing a high purity of glutamic acid. The glutamate-comprising aqueous feed may need some dilution. Water introduced for that purpose would mainly end up in the aqueous effluent from the process, and would increase the load on the final treatment of the latter. This can be avoided by using a part of the effluent from step (d) which is recycled to dilute the glutamate-comprising aqueous feed to the process. This effluent from step (d) can also be used for sweetening off the resin prior to elution.

Steps (a) and (b) are performed at an elevated temperature to avoid crystallization of liberated glutamic acid on the resins. The temperature in these steps is preferably between 55 and 80° C., and more preferably between 65 and 78° C.

In a preferred embodiment of the present invention, the glutamic acid crystallized in step (c) is neutralized by an NaOH solution and monosodium glutamate (MSG) is crystallized from the solution obtained.

In another preferred embodiment of the present invention, mother liquor from MSG crystallization comprises at least part of the aqueous feed to step (a).

Especially preferred is said embodiment wherein the mother liquor is obtained in a process, wherein the glutamic acid crystallized in step (c) is neutralized by an NaOH solution and monosodium glutamate (MSG) is crystallized from the solution obtained.

The present invention is especially applicable since the content of impurities resulting from fermentation in the salt solution of step (h) is low and said solution is utilized by crystallizing valuable salts therefrom.

In an especially preferred embodiment of the present invention the aqueous feed stream is diluted and this is preferably achieved by recycling a part of the effluent of step (d) to the aqueous feed stream.

In a most preferred embodiment of the present invention, the salts content of the effluent of step (d) is low and part of this stream is used in an animal feed composition, and this especially wherein the aqueous feed to step (a) comprises cells resulting from the fermentation, which cells remain after the process and are utilizable for this purpose.

The solution obtained in regeneration of the resins (the effluent of step (g)), contains the salts obtained from the cations removed from the aqueous feed to the process and the anion of the regenerating strong acid. These components are designed so that the salt obtained has a positive value and could be further utilized. Thus, if ammonium is present in the aqueous feed to the process, the salts obtained, e.g. ammonium sulfate, phosphate or chloride could be used as fertilizers.

In another preferred embodiment the salt is used as a nutrient or a reagent in a fermentation process. These salt solutions are also obtained in processes recovering glutamic acid by direct acidulation of the glutamate-containing feed. However, in the present invention the salt solution is much more concentrated (its concentration is, in fact, determined by the concentration of the strong acid used for regeneration), and contains much less impurities. It therefore can be utilized as such, or subjected to a crystallization operation to recover the salts in a crystaline form.

The regenerating acid can be any strong, preferably mineral acid, e.g., HCl, $H_2SO_4$, $H_3PO_4$ and their mixtures. Note that while phosphoric acid would not be considered in prior art processes based on SACE only, it could be used in the regeneration step of the present process.

The glutamate-containing feed stream contains carbohydrates, carboxylic and amino acids, and other organic, non-fermentables. These compounds are valuable as animal feed components. In the direct acidulation processes, these components are obtained in the mother liquor of glutamic acid crystallization, together with dissolved glutamic acid salts. Their recovery is tedious and expensive in equipment, energy and reagents. In the process of this invention, these components are obtained in the effluent of step (d), essentially free of glutamic acid and salts, and are easily applicable in animal feed. This effluent from step (d) would also contain cells that were introduced with the glutamate-containing feed to the process. Those cells can be added to the animal feed.

As described above, the combination of SACE and WACE avoids the need of high excess of regenerating acid. The amount of acid utilized in the process is preferably 130 equivalents per 100 total equivalents of cations bound to the resins, and more preferably 115 equivalents.

In the process of the present invention, the conditions are preferably optimised so that overall glutamic acid recovery from the aqueous feed is above 98% and the purity of glutamic acid obtained in step (c) is also above 98%

It should be noted that a surprising and unexpected feature of the present invention was the discovery that at least 50% of the cations are adsorbed on said weak acid cation exchanger, and that in preferred embodiments of the present invention at least 75% of the cations are adsorbed on said weak acid cation exchanger.

Furthermore, it was surprising and unexpected to discover that in carrying out the novel process of the present invention, 2 liters of said weak acid cation exchanger adsorb at least 1 mole of cations.

Certain preferred embodiments of the invention will now be described in the following examples.

EXAMPLE 1

Fermentation broths were produced using a selected strain and starch hydrolysate as the main feedstock, pH was regulated with ammonia.

The average analysis of the broths was as set forth below:

| BROTH | concentration g/L | nitrogen g/L | mequ./L |
|---|---|---|---|
| Bacteria cells | 17.25 | 2.24 | — |
| Glutamic acid | 115.00 | 10.95 | 782 |
| Organic matters | 40.46 | 0.72 | 70 |
| Ammonia | 14.38 | 11.84 | 846 |
| SO4 | 1.24 | — | 26 |
| PO4 | 0.91 | — | 10 |
| Cl | 0.69 | — | 19 |
| Na | 0.68 | — | 30 |
| K | 0.66 | — | 17 |
| Mg | 0.12 | — | 10 |
| Ca | 0.09 | — | 4 |

The broths were separated by ultrafiltration.

The broths were separated on tubular organic membranes from PCI with average flow rate of 140 liter/h.sqm, at 70° C. with volume concentration ratio of 5, i.e. for 5 volumes of broth 4 volumes of permeate and 1 volume of retentate were obtained.

The PCl membrane has a 200,000 dalton cutoff.

The average analysis were as follows:

| PERMEATE | concentration g/L | nitrogen g/L | mequ./L |
|---|---|---|---|
| Glutamic acid | 116.44 | 11.09 | 792 |
| Organic matters | 40.96 | 0.73 | 70 |
| Ammonia | 14.56 | 11.99 | 856 |
| SO4 | 1.26 | — | 26 |
| PO4 | 0.93 | — | 10 |
| Cl | 0.70 | — | 20 |
| Na | 0.69 | — | 30 |
| K | 0.67 | — | 17 |
| Mg | 0.12 | — | 10 |
| Ca | 0.09 | — | 4 |

| RETENTATE | Concentration g/L | nitrogen g/L | mequ./L |
|---|---|---|---|
| Bacteria cells | 86.25 | 11.21 | — |
| Glutamic acid | 109.25 | 10.4 | 743 |
| Organic matters | 38.43 | 0.68 | 66 |
| Ammonia | 13.66 | 11.25 | 803 |
| SO4 | 1.18 | — | 25 |
| PO4 | 0.87 | — | 9 |
| Cl | 65 | — | 18 |
| Na | 0.65 | — | 28 |
| K | 0.63 | — | 16 |
| Mg | 0.11 | — | 10 |
| Ca | 0.08 | — | 4 |

In a first experiment, 1.5 liter of permeate containing 1310 meq of mineral cation was fed at 75° C. on a 1 liter column of IMAC HP336 resin from RHOM and HASS, which resin is a weak acid cation exchanger in acid form.

The feeding flow rate was 6 liters per hour.

The resin was then sweetened off with water at the same flow rate and the solution obtained was combined with the effluent.

2.5 liters of solution were obtained at pH 3.5 at 75° C.

This solution was cooled down to 20° C. and maintained for 2 hours at said temperature.

Crystallized glutamic acid was separated by filtration and washed with the same amount of water.

123 g of dry glutamic acid crystal with 98% purity and 2.5 liters of mother-liquor with a glutamic acid concentration of 20 g/l was obtained.

The crystallization yield was 69%.

EXAMPLE 2

2 liters of the crystallization mother-liquor obtained in Example 1 was fed at 75° C. to a column containing 0.4 liter of a strong acid cation exchanger in H+ form, (C20 resin from RHOM and HASS) at a flow rate of 2.4 liter per hour.

The resin was then sweetened off with water at the same flow rate and the solution obtained was combined with the effluent.

The effluent was analysed and found to be free of glutamic acid and cation, pH of the effluent was 1.3.

Thus, 50 g of glutamic acid was loaded on the SACE column.

EXAMPLE 3

0.4 liter of permeate were diluted with 0.6 liter of effluent obtained in Example 2, the obtained solution was percolated at 75° C. on the 0.4 liter SACE column loaded with glutamic acid in Example 2.

The feed flow rate was 2.4 liter per hour.

The resin was then sweetened off with water at the same flow rate and the solution obtained was combined with the effluent.

The combined solution had a pH of 3.2; 97 g of glutamic acid were measured in the effluent; and, all glutamic acid loaded on the SACE in Example 2 was eluted in the last effluent.

Glutamic acid was crystallized by cooling the effluent down to 20C during 3 hours.

62 g of glutamic acid were obtained with a 98% purity and a recovery yield of 67%.

What is claimed is:

1. An indirect acidulation process for producing glutamic acid comprising the steps of:

(a). contacting an aqueous feed stream containing glutamate resulting from fermentation at a temperature of between 55° C. and 80° C., with a weak acid cation exchanger (WACE) which is at least partially in its acid form, whereby part of the cations in the solution are taken up by the cation exchanger and protons are introduced into the solution;

(b). contacting a second aqueous feed containing glutamate and cations, at a temperature of between 55° C. and 80° C., with a strong acid cation exchanger (SACE) that is obtained from a subsequent step and carries cationic glutamate, whereby the cationic glutamate is transferred into the solution and most of said cations in said second aqueous feed are taken up by the SACE;

(c). crystallizing glutamic acid from the effluent of step (b);

(d). contacting the mother liquor of step (c) with an SACE which is at least partially in its acid form, whereby cationic glutamate is bound;

(e). utilizing the SACE obtained in step (d) in step (b);

(f). regenerating the SACE from step (b) to its at least partially acid form by a solution of a strong acid and utilizing the SACE in its at least partially acid form in step (d) while forming an effluent containing an acidic solution of salts, comprising cations bound to the cation exchanger in step (b) and the anions of the strong acid;

(g). regenerating the WACE from step (a) to its at least partially acid form by the effluent from step (f) and utilizing the WACE in its at least partially acid form in step (a) while forming an effluent containing a solution of salts, comprising cations bound to the cation exchangers in steps (a) and (b) and the anions of the strong acid;

(h). directing the salt solution obtained as he effluent of step (g) for commercial use.

2. A process according to claim 1, wherein the glutamic acid crystallized in step (c) is neutralized by a NaOH solution and monosodium glutamate (MSG) is crystallized from the solution obtained.

3. A process according to claim 2, wherein the mother liquor from MSG crystallization comprises at least part of the aqueous feed to step (a).

4. A process according to claim 3, wherein the mother liquor is obtained in a process wherein the glutamic acid crystallized in step (c) is neutralized by an NaCH solution and monosodium glutamate (MSG) is crystallized from the solution obtained.

5. A process according to claim 1, wherein at least one of the aqueous feed streams is diluted.

6. A process according to claim 1, wherein part of the effluent of step (d) is recycled to dilute the aqueous feed stream.

7. A process according to claim 1, wherein the effluent of step (d) is used in an animal feed composition.

8. A process according to claim 1, wherein the aqueous feed to step (a) comprises cells resulting from the fermentation.

9. A process according to claim 8, wherein a glutamate-containing fermentation liquor is treated to form two streams, a first stream substantially free of cells and second stream comprising most of the cells present initially in the fermentation broth, said second stream being fed as the aqueous feed stream to step (a).

10. A process according to claim 8, wherein most of the cells present initially in the aqueous feed to step (a) are present in the effluent from step (d), and are used in an animal feed composition.

11. A process according to claim 1, wherein the acidulation process is optimized such that the overall glutamic acid recovery from the aqueous feed is above 98%.

12. A process according to claim 1, wherein the acidulation process is optimized such that the purity of glutamic acid obtained in step (c) is above 98%.

13. A process according to claim 1, wherein the temperature in steps (a) and (b) is between 65 and 78° C.

14. A process according to claim 1, wherein the amount of acid utilized is 130 equivalents per 100 total equivalents of cations bound to the resins.

15. A process according to claim 1, wherein the amount of acid utilized is 115 equivalents per 100 total equivalents of cations bound to the resins.

16. A process according to claim 1, wherein said second aqueous feed which is contacted with the SACE in step (b) comprises effluent from step (a).

17. A process according to claim 1, wherein at least 50% of the cations are adsorbed on said weak acid cation exchanger in step (a).

18. A process according to claim 1, wherein at least 75% of the cations are adsorbed on said weak acid cation exchanger in step (a).

19. A process according to claim 1, wherein 2 liters of said weak acid cation exchanger adsorb at least 1 mole of cations.

20. A process according to claim 1, wherein at least part of the cations absorbed on said WACE in step (a) are removed by contacting said WACE with $CO_2$ as a regenerating agent.

21. A process according to claim 1, wherein at least one of steps (a), (b), (d), (f), or(g) is conducted in a multi-stage mode.

22. A process according to claim 1, wherein at least one of steps(a),(b), (d), (f), or (g) is conducted in a counter-current mode.

23. A process according to claim 1, wherein all of steps(a), (b), (d), (f), and (g) are conducted in a multi-stage, counter-current mode.

* * * * *